(12) United States Patent
Pretz (10) Patent No.: US 10,227,271 B2
(45) Date of Patent: Mar. 12, 2019

(54) INTEGRATED C3—C4 HYDROCARBON DEHYDROGENATION PROCESS

(71) Applicant: Dow Global Technologies LLC, Midland, MI (US)

(72) Inventor: Matthew T. Pretz, Lake Jackson, TX (US)

(73) Assignee: Dow Global Technologies LLC, Midland, MI (US)

( * ) Notice: Subject to any disclaimer, the term of this patent is extended or adjusted under 35 U.S.C. 154(b) by 0 days.

(21) Appl. No.: 15/561,381

(22) PCT Filed: Mar. 7, 2016

(86) PCT No.: PCT/US2016/021127
§ 371 (c)(1),
(2) Date: Sep. 25, 2017

(87) PCT Pub. No.: WO2016/160273
PCT Pub. Date: Oct. 6, 2016

(65) Prior Publication Data
US 2018/0079700 A1   Mar. 22, 2018

Related U.S. Application Data

(60) Provisional application No. 62/139,938, filed on Mar. 30, 2015.

(51) Int. Cl.
*C07C 5/327* (2006.01)
*C07C 5/333* (2006.01)
(Continued)

(52) U.S. Cl.
CPC .............. *C07C 5/3332* (2013.01); *B01J 21/04* (2013.01); *B01J 21/12* (2013.01); *B01J 23/26* (2013.01);
(Continued)

(58) Field of Classification Search
CPC ................................. C07C 5/327; C07C 5/333
(Continued)

(56) References Cited

U.S. PATENT DOCUMENTS 4,482,451 A   11/1984  Kemp
4,579,716 A    4/1986  Krambeck et al.
(Continued)

FOREIGN PATENT DOCUMENTS

EP   0637578 A1   11/1993
EP   1261219 A2    5/2002
(Continued)

OTHER PUBLICATIONS

Geldart; Types of Gas Fluidization; Power Technology; 1973, 285-292, vol. 7; Elsevier Sequoia, Lausanne, Netherlands.
(Continued)

*Primary Examiner* — Thuan D Dang
(74) *Attorney, Agent, or Firm* — Dinsmore & Shohl

(57) ABSTRACT

An integrated process, suitable for use in a new or retrofitted plant, produces an olefin or di-olefin via the dehydrogenation of an appropriate C3-C4 hydrocarbon feed includes (1) contacting the feed and a dehydrogenation catalyst having a Geldart A or Geldart B classification in a fluidized bed at a temperature from 550° C. to 760° C. and a pressure from about 41.4 to about 308.2 kPa (about 6.0 to about 44.7 psia) and a catalyst to feed ratio, w/w, from 5 to 100 to form a dehydrogenate product; separating the dehydrogenate product and unreacted starting feed mixture from a portion of the catalyst by means of a cyclonic separation system; reactivating the catalyst in a fluidized regenerator by combustion at 660° C. to 850° C., followed by contact with an oxygen-containing fluid at 660° C. or greater, and returning the catalyst to the dehydrogenation reactor; (2) compressing the product mixture to form a compressed product mixture; and
(Continued)

OPTION 1

OPTION 2

(3) fractionating the compressed product mixture to form a product stream including at least the target olefin or di-olefin. The integrated process offers increased plant capacity, improved economics, and reduced environmental impact in comparison with other known and conventional processes.

12 Claims, 3 Drawing Sheets

(51) Int. Cl.
| | |
|---|---|
| B01J 38/02 | (2006.01) |
| B01J 38/12 | (2006.01) |
| B01J 38/14 | (2006.01) |
| B01J 23/62 | (2006.01) |
| B01J 23/94 | (2006.01) |
| B01J 35/00 | (2006.01) |
| B01J 21/04 | (2006.01) |
| B01J 21/12 | (2006.01) |
| B01J 23/26 | (2006.01) |
| B01J 23/887 | (2006.01) |
| B01J 23/92 | (2006.01) |
| B01J 23/96 | (2006.01) |
| B01J 35/10 | (2006.01) |

(52) U.S. Cl.
CPC .......... *B01J 23/62* (2013.01); *B01J 23/8871* (2013.01); *B01J 23/92* (2013.01); *B01J 23/94* (2013.01); *B01J 23/96* (2013.01); *B01J 35/0006* (2013.01); *B01J 35/1009* (2013.01); *B01J 35/1014* (2013.01); *B01J 38/02* (2013.01); *B01J 38/12* (2013.01); *B01J 38/14* (2013.01); *C07C 2521/04* (2013.01); *C07C 2521/08* (2013.01); *C07C 2521/12* (2013.01); *C07C 2523/08* (2013.01); *C07C 2523/42* (2013.01); *C07C 2523/62* (2013.01); *Y02P 20/125* (2015.11); *Y02P 20/52* (2015.11); *Y02P 20/584* (2015.11)

(58) Field of Classification Search
USPC ................ 585/659, 660, 661, 627, 628, 629
See application file for complete search history.

(56) References Cited

U.S. PATENT DOCUMENTS

| | | | |
|---|---|---|---|
| 4,588,558 | A | 5/1986 | Kam et al. |
| 4,746,643 | A | 5/1988 | Buonomo et al. |
| 5,177,293 | A | 1/1993 | Mitariten et al. |
| 5,190,650 | A | 3/1993 | Tammera et al. |
| 5,227,566 | A | 7/1993 | Cottrell et al. |
| 5,227,567 | A | 7/1993 | Mitariten et al. |
| 5,275,641 | A | 1/1994 | Tammera et al. |
| 5,315,056 | A | 5/1994 | Feldman et al. |
| 5,430,211 | A | 7/1995 | Pogue et al. |
| 5,457,077 | A | 10/1995 | Williamson et al. |
| 6,031,143 | A | 2/2000 | Buonomo et al. |
| 6,362,385 | B1 | 3/2002 | Iezzi et al. |
| 7,429,363 | B2 | 9/2008 | Yuan et al. |
| 8,563,793 | B2 | 10/2013 | Zimmermann et al. |
| 8,669,406 | B2 | 3/2014 | Pretz et al. |
| 8,927,799 | B2 | 1/2015 | Myers et al. |
| 2004/0242945 | A1 | 12/2004 | Pelati et al. |
| 2014/0056737 | A1 | 2/2014 | Panambur et al. |
| 2014/0060371 | A1 | 3/2014 | Kim et al. |
| 2014/0068271 | A1 | 3/2014 | Hird et al. |
| 2015/0065471 | A1 | 3/2015 | Puig Duran et al. |

FOREIGN PATENT DOCUMENTS

| | | |
|---|---|---|
| GB | 1107432 | 3/1968 |
| WO | 9523123 A1 | 8/1995 |
| WO | 02096844 A1 | 12/2002 |
| WO | 03053567 A2 | 7/2003 |
| WO | 2010107591 A1 | 9/2010 |
| WO | 2013009820 A1 | 1/2013 |
| WO | 2013126210 A1 | 8/2013 |
| WO | 2014043638 A2 | 3/2014 |

OTHER PUBLICATIONS

Geldart; Gas Fluidization Technology; 1987, 38-48, Section 3.3; John Wiley & Sons. Chichester, New York.
International Search Report and Written Opinion PCT/US2016/021127, dated May 7, 2016.

Figure 1.

Geldart Fluidization Diagram: Groups A-D.

Key:
$\rho_p$ is particle density of the solids (g/cm$^3$)
$\rho_g$ is gas density (g/cm$^3$)
$d_p$ is mean particle diameter (μm)
*Line separating B and D is represented by the equation $(\rho_p - \rho_g)(d_p)^2 \geq 10^6$. (I.e., to be in Group B, the catalyst must have a $(\rho_p - \rho_g)(d_p)^2 < 10^6$.)
**Line separating A and B is represented by the equation $(\rho_p - \rho_g)(d_p)^2 \leq 225$.
***Shaded line separating A and C is represented by the equation $U_{mb}/U_{mf} \geq 1$, where $U_{mb}$ is the superficial velocity of the carrier gas at minimum bubbling separating conditions, and $U_{mf}$ is the superficial velocity of the carrier gas at minimum fluidization, both in cm/s. (I.e., to be in Group A, the catalyst must satisfy the equation.)

Figure 2.

OPTION 1

OPTION 2

Figure 3.

INTEGRATED C3—C4 HYDROCARBON DEHYDROGENATION PROCESS

The present application claims the benefit of U.S. Patent Application Ser. No. 62/139,938, filed on Mar. 30, 2015, entitled "INTEGRATED C3-C4 HYDROCARBON DEHYDROGENATION PROCESS," which is incorporated by reference herein in its entirety.

This invention relates to the field of hydrocarbon conversion processes and particularly to the dehydrogenation of lower hydrocarbons. More particularly, the invention relates to the dehydrogenation of lower paraffins to form their corresponding olefins, or of lower olefins to form their corresponding di-olefins.

A number of lower olefins and di-olefins are known to be widely used in a variety of chemical processes, both as starting materials and as intermediates. These may include, in non-limiting example, propylene, butene, iso-butene, and butadiene. Among these, propylene is a particularly sought chemical that finds use in a variety of applications, particularly as an intermediate. Among these applications are production of polypropylene, acrylonitrile, oxo chemicals, propylene oxide, cumene, isopropyl alcohol, acrylic acid, polygas chemicals, plastics such as acrylonitrile-butadiene-styrene, propylene glycols for, for example, paints, household detergents and automotive brake fluids, and polyurethane systems for, for example, rigid foam insulation and flexible foams. Propylene is also produced and consumed in refinery operations for the production of gasoline components.

Generally there are five methods of producing propylene. They are steam cracking, fluid catalytic cracking, propane dehydrogenation, a natural gas- or methanol-to-olefins process, and olefin conversion. One of the most common means of producing propylene is as a by-product of ethylene production via steam cracking of propane or naphtha or as a by-product of fluidized catalytic cracking (FCC). However, because of the relatively recent and substantial availability of shale gas, an increased volume of ethylene can now be produced via steam cracking of ethane, a process that results in only small amounts of propylene. This is at odds with the fact that demand for propylene continues to increase, resulting in a supply/demand imbalance. The cyclic nature of the chemical industry suggests that this propylene shortfall will continue to occur on at least an intermittent basis. Consequently, "on-purpose" production of propylene via dehydrogenation of propane is increasingly attractive.

One route to propylene that has been well-explored by researchers has been to dehydrogenate propane, or to state it more broadly, to dehydrogenate a paraffin, often in the form of a light paraffins mixture, to form the corresponding olefin, again often as a constituent of a light olefins mixture. Such dehydrogenation on a commercial scale requires large and complex plants to accommodate myriad process variables.

One well-known "on-purpose" process to produce propylene, which is generally referred to as "the OLEFLEX™ process" (OLEFLEX is a trademark of UOP Inc.) or "the OLEFLEX™ reaction system," employs multiple adiabatic reactors arranged in a series, wherein propane dehydrogenation is catalyzed by the presence of a proprietary catalyst which is typically platinum on alumina. Interheaters are used between reactors in order to maintain the desired reactor temperatures, which accommodates the endothermic dehydrogenation reaction. Hydrogen, sulfur or both are injected into the reactor system to suppress the formation of coke. A regenerator, referred to as a "CCR™" (CCR is a trademark of UOP Inc.), is employed for catalyst reactivation via injection of air and chlorine or a chlorine-containing compound, which serves to burn coke and redisperse the catalyst's platinum. Reactor by-products, which may include small amounts of ethylene, ethane and methane, may be used to supplement the fuel consumption for the unit. Hydrogen resulting from the dehydrogenation is recycled, recovered, or used as fuel.

Another aspect of the OLEFLEX™ reaction system, as well as other "on purpose" propylene processes, is that they are generally used in conjunction with a compressor and a "product recovery unit" (PRU). The compressor increases the pressure of the product mixture exiting the reactor, which facilitates cryogenic separation of the target product and unreacted feed. A typical PRU employs a multi-column fractionation train which may include, for example, a depropanizer, a deethanizer, one or two separation columns, a drier, a treater, a caustic tower, a hydrogenation reactor, a cold box and turboexpander, a pressure swing adsorber (PSA), and/or potentially other components. Each part of such a process is designed to enable or facilitate fractionation of the product and enable production of at least a single target olefin or di-olefin.

The various aspects of many systems designed to carry out dehydrogenation to produce target olefins or di-olefins, including but not limited to aspects that may be part of some embodiments of the OLEFLEX™ reaction system, are disclosed in a number of publications. These may include, for example, U.S. Pat. No. 5,227,566 (process for the dehydrogenation of hydrocarbons); U.S. Pat. No. 5,457,077 (moving bed regeneration process with combined drying and dispersion steps); U.S. Pat. No. 5,177,293 (separation process for the product streams resulting from the dehydrogenation of hydrocarbons); U.S. Pat. No. 5,227,567 (separation process for the product streams resulting from the dehydrogenation of hydrocarbons); and U.S. Pat. No. 8,563,793 (propylene recovery unit). OLEFLEX™ information, per se, may also be found in the OLEFLEX™ brochure dated 2007, available from UOP, Inc.

It is noted that, wherever a parenthetical word or phrase is included following identification of a patent or patent publication in this specification, such is included for purposes of reader convenience only and does not constitute actual or precise summarizations or descriptions of the scope or teaching of the referenced specification or of any claims included therein. In some cases, parenthetical references to "Dow" refer to The Dow Chemical Company and/or a subsidiary thereof as the assignee or owner of the patent or patent publication indicated. Parenthetical references to "Snamprogetti" refer to Snamprogetti S.p.A. and/or a subsidiary thereof in the same role, as an assignee or owner.

Disadvantages of the OLEFLEX™ reaction system, however, may include use of catalysts containing relatively high levels of platinum, thereby ensuring relatively high cost; embrittlement of stainless steel reactors by the chlorine used in catalyst reactivation; and cracking and creep of the reactor materials. Furthermore, the OLEFLEX™ process includes substantial heat generation for the reactors at flame temperature, which generates significant nitrogen oxides (NOx) emissions, which may require NOx control capital to mitigate.

Another well-known "on-purpose" process to produce propylene, which is generally referred to as "the CATOFIN™ process" (CATOFIN is a trademark of Chicago Bridge and Iron, Inc.) or "the CATOFIN™ reaction system," includes multiple fixed bed dehydrogenation reactors deployed in parallel. This reaction system accomplishes dehydrogenation using a chromium-containing catalyst. Aspects of the CATOFIN™ process are described in detail in, for example, WO1995023123 (endothermic catalytic dehydrogenation process); U.S. Pat. No. 5,315,056 (catalyst regeneration in a dehydrogenation process); and a CATOFIN™ brochure dated 2007. Disadvantages of the CATOFIN™ process include the need for a relatively high catalyst inventory due to its use of a fixed bed configuration; and the requirement for high frequency, high temperature valves for swapping the fixed beds. Again, as with the OLEFLEX™ process, CATOFIN™ includes substantial heat generation via thermal combustion, which generates undesirably high levels of NOx emissions.

Another type of dehydrogenation reactor is described in U.S. Pat. No. 8,669,406 (Dow). In this reactor a fluidized catalyst bed that rises with the propane feedstock flow is employed. U.S. Pat. No. 5,430,211 (Dow) describes a dehydrogenation catalyst comprising a mordenite zeolite, further optionally including gallium, zinc or a platinum group metal. Additional research in this area is reflected in WO2014/043638 (Dow, reactor and feed distributor); PCT/US14/060371 (Dow, quench exchanger); PCT/US14/056737 (Dow, cyclone plenum); PCT/US14/068271 (Dow, sulfur management); PCT/US15/065471 (Dow, riser guide); WO2013/126210 (Dow, reconstituted catalyst); U.S. Pat. No. 6,362,385 (Snamprogetti, bubbling bed reactor and regeneration system); U.S. Pat. No. 4,746,643 (Snamprogetti, chromium-based catalyst); and U.S. Pat. No. 7,235,706 (Snamprogetti, dehydrogenation process).

Despite the above-described advances in the field of plant-scale dehydrogenation processes, it is clear that there remains room for improvements that overcome the various disadvantages and shortcomings of presently practiced technologies, including but not limited to those generally understood to represent the prior art OLEFLEX™ and prior art CATOFIN™ reaction systems. More particularly, it would be advantageous if new processes were disclosed that were suitable or adaptable for use in a pre-existing dehydrogenation facility, wherein such could be used to increase capacity, reduce energy requirements, or both, and the pre-existing facility could be thereby made to operate more efficiently and/or more economically.

In one aspect the invention provides an integrated process for producing C3-C4 olefins or C3-C4 di-olefins comprising the steps of: (1) (a) contacting, in a fluidized dehydrogenation reactor, (i) a C3-C4 hydrocarbon feed and (ii) a catalyst feed comprising a catalyst meeting the requirements of a Geldart A or Geldart B classification; at a ratio of catalyst feed to C3-C4 hydrocarbon feed of from 5 to 100 on a weight to weight basis; wherein optionally the C3-C4 hydrocarbon feed and the catalyst feed have been preheated to a temperature of from about 400° C. to about 660° C.; and wherein the average contact time between the C3-C4 hydrocarbon feed and the catalyst feed is from about 1 second to about 10 seconds; and wherein the reaction temperature in the fluidized dehydrogenation reactor is from about 550° C. to about 750° C.; and wherein the pressure in the fluidized dehydrogenation reactor is from 6.0 to 44.7 pounds per square inch absolute at the outlet of the reactor; under conditions such that a step (1)(a) product mixture, comprising a C3-C4 target olefin or di-olefin, hydrogen and unreacted C3-C4 hydrocarbon feed, is formed; and the catalyst has coke deposited thereon and is at least partially deactivated such that it forms an at least partially deactivated catalyst; and (b) transferring the step (1)(a) product mixture and the at least partially deactivated catalyst from the fluidized dehydro-generation reactor to a cyclonic separation system, and optionally cooling the step (1)(a) product mixture and the at least partially deactivated catalyst to a temperature lower than the reaction temperature, such cooling occurring before, after, or both before and after, the transfer thereof to the cyclonic separation system; under conditions such that (i) the step (1)(a) product mixture and the at least partially deactivated catalyst remain in contact, at the reaction temperature and after the transfer to the cyclonic separation system, for an average time of from 0 seconds to less than about 10 seconds, and (ii) the step (1)(a) product mixture is converted to form a step (1)(b) product mixture; and thereafter substantially separating the step (1)(b) product mixture and the at least partially deactivated catalyst from each other; (c) transferring at least a portion of the at least partially deactivated catalyst to a regenerator vessel and heating the at least partially deactivated catalyst therein to a combustion temperature of from about 660° C. to about 850° C. in order to combust the coke deposited on the at least partially deactivated catalyst therein, using heat generated by the coke combustion itself and also by a supplemental fuel, the heating forming a heated, further deactivated catalyst which has an activity for dehydrogenating the C3-C4 hydrocarbon feed that is less than that of the at least partially deactivated catalyst, and, (d) subjecting the heated, further deactivated catalyst to a conditioning step, comprising maintaining the heated, further deactivated catalyst at a temperature of at least 660° C. under a flow of an oxygen-containing gas for more than 2 minutes, to form an oxygen-containing, at least partially reactivated catalyst that has an activity for dehydrogenating the C3-C4 hydrocarbon feed that is greater than that of the at least partially deactivated catalyst; and (e) transferring the at least partially reactivated catalyst back to the fluidized dehydrogenation reactor; (2) transferring the step (1)(b) product mixture to a compressor, wherein the step (1)(b) product mixture is compressed at least once to form a step (2) product mixture; and (3) transferring the step (2) product mixture to a product recovery area, wherein the step (2) product mixture is separated into recovered products comprising at least one or more target C3-C4 olefin or di-olefin fractions, and, optionally, one or more additional fractions selected from an unreacted C3-C4 hydrocarbon feed fraction; a light gas fraction; a heavies fraction; a by-products fraction; and combinations thereof; and wherein optionally at least a portion of the optional unreacted C3-C4 hydrocarbon feed fraction is recycled back to step (1)(a); and wherein optionally one or more of the recovered products is transferred to a second product recovery unit and the step (3) separation is repeated therein; and wherein optionally the optional light gas fraction is transferred to step (1)(c) to serve as the supplemental fuel.

The process of the present invention may be employed either in a plant that has been designed specifically for it, or in a plant previously designed to carry out another dehydrogenation process, such as, but not limited to, installation of an OLEFLEX™ or CATOFIN™ reaction system. In the latter case, the plant can be retrofitted such that, instead of the designed-for process occurring therein, the process of the present invention is carried out therein. In the event of a retrofit, the plant capacity of the existing equipment may be increased in an amount of at least 5 percent (%), and in some embodiments at least 10%, by use of the inventive process, in comparison with that of the non-retrofitted plant. The increased capacity is brought about by the inventive integrated process that offers improved operating conditions and, in certain embodiments, synergistic efficiency to bring about unexpected improvements in conversions and selectivity. Alternatively, the retrofitted plant can operate at lower energy usage per pound of target product, for example, propylene, due to the novel and inventive combination of operating means, parameters, and process flow that result in significantly greater efficiency than a non-retrofitted or other plant designed for another dehydrogenation process.

The inventive process includes, in general, three steps. These parts are defined herein, for convenience of discussion only, as comprising (1) reaction and catalyst reactivation; (2) compression; and (3) separation. Each of these parts is described in detail hereinafter.

1. Reaction and Catalyst Reactivation

Step (1) described herein is the reaction and catalyst reactivation. While this phrase suggests, and does represent, two separate sub-processes, the sub-processes are combined for discussion purposes herein because, in a preferred embodiment of a facility designed or retrofitted to carry out the inventive process, they would be anticipated to generally occur concurrently and in close physical proximity. This process step (1) includes, in one aspect, contacting a selected C3-C4 hydrocarbon feed and a suitable dehydrogenation catalyst.

As defined herein, the C3-C4 hydrocarbon feed comprises at least one hydrocarbon selected from C3, C4, or a combination thereof. For convenience, any of these embodiments is generally comprehended within the term "C3-C4 hydrocarbon feed." Such desirably primarily, predominantly, or substantially comprises the C3 and/or C4 compound that can be most directly dehydrogenated to form the desired target olefin or di-olefin. Accordingly, it is generally preferred that a linear C3 and/or C4 paraffin or olefin be employed. It will, however, be understood by those skilled in the art that, because of various processing variables that may be encountered, particularly at commercial scale, the presence of a small proportion of non-linear, e.g., aromatic and/or cyclic, compounds may be present in the C3-C4 hydrocarbon feed, as well as linear, aromatic, and/or cyclic C1-C2 and/or C4+ compounds, as will be discussed in greater detail hereinafter. In general it is preferred that such additional components be limited to amounts less than 10 weight percent (wt %), more preferably less than 5 wt %.

For example, it is desirable, where the target product is an olefin (as distinguished from a di-olefin), that the C3-C4 hydrocarbon feed comprises the corresponding, i.e., same carbon number, starting paraffin, preferably in rich amount. As the term is used herein, "rich amount" means a feed comprising at least 50 percent by weight (wt %) of such paraffin, preferably at least 80 wt %, and most preferably at least 90 wt %. More specific examples of this include propane, to produce propylene; butane, to produce butylene [alternatively termed butene]; and iso-butane, to produce iso-butene. If the target product is a di-olefin, it is desirable that the C3-C4 hydrocarbon feed comprises the corresponding starting olefin, again preferably in rich amount. A more specific example of this is butene, to produce butadiene. The C3-C4 hydrocarbon feed as defined may be obtained via recycle of unreacted starting paraffin or starting olefin from a later part of the inventive process, as described in greater detail hereinbelow, but also may be simply a selected fresh feed that may be, in one embodiment, the desired starting paraffin or olefin per se. In most embodiments it is a combination of recycled, unreacted C3-C4 starting paraffin or olefin, or a fraction containing both in some relative proportion, and fresh C3-C4 starting paraffin or olefin.

In the inventive process the contact is carried out under relatively short contact times in order to prevent undesirable side reactions and product degradation. The term "average contact time" or "contact time" as used herein is intended to refer to the time in which the molar average of gaseous C3-C4 hydrocarbon feed molecules is in contact with the catalyst while at reaction temperature, regardless of whether the feed is converted to one or more desired products. The term "reaction temperature" is intended to mean a temperature at which a significant amount of chemical reaction occurs, regardless of whether such reaction is the desired dehydrogenation of the C3-C4 hydrocarbon feed to its target product. Said another way, the reaction temperature is the temperature at which the starting C3-C4 hydrocarbon molecules are no longer thermally stable. The term "significant amount" is intended to mean a detectable amount having an economic impact on the process, and is herein further defined as an amount of at least 0.5 wt % per second of the starting C3-C4 feed is converted to at least one product compound.

In most embodiments of the invention, the reaction temperature is greater than 500° C. and preferably greater than 550° C. In particular embodiments the reaction temperature is from 500° C., preferably 550° C., more preferably 570° C., to 760° C. The temperature may be measured with at least two thermocouples, the first of which is located where the hydrocarbon feed and catalyst feed are understood, in view of the knowledge of the skilled practitioner and the known design of the dehydrogenation reactor, to be initially contacting one another, and the second of which is located where the starting C3-C4 hydrocarbon feed and the catalyst are no longer in contact at all, or no longer in contact at the reaction temperature, i.e., the feed and catalyst have just been separated, and/or the feed and catalyst have just been quenched to a temperature below the reaction temperature, as discussed in further detail hereinbelow. Thus, these thermocouples (and in many designs additional thermocouples serving to monitor temperature throughout the dehydrogenation system) are important to ensure that the contact times at reaction temperature meet the requirements taught herein.

The general goal is to employ an average contact time that is sufficiently long to dehydrogenate acceptable amounts of the starting C3-C4 hydrocarbon feed, but is not so long as to result in unacceptable amounts of by-products. While the required contact time is related to the specific feed, catalyst(s) and reaction temperature(s), in particular embodiments of the invention the contact time within the dehydrogenation reactor is less than 60 seconds, preferably less than 10 seconds, more preferably less than 8 seconds, and still more preferably less than 7 seconds. Contact times may therefore range from about 0.5, or about 1, to about 10 seconds, preferably from about 0.5, or about 1, to about 8 seconds, and more preferably from about 0.5, or about 1, to about 7 seconds. In order to achieve high conversions due to the equilibrium constraints of the dehydrogenation reactions, the reactor must operate at a temperature in which the gas phase thermal reaction rate is significant. This means that, if the thermal reaction is occurring at a rate of greater than 0.5 wt % of the C3-C4 feed per second, it is necessary, in order to ensure meeting the contact time limitations hereinabove, to design a reaction system having an appropriate diameter and length at the target feed rate and product rate to achieve a highly productive reactor. Further detail concerning application of the separation device is provided hereinafter.

Due to the active nature of the preferred catalysts, the average residence time of the catalyst within the dehydrogenation reactor is preferably less than about 240 seconds, preferably from about 5 seconds to about 200 seconds, more preferably from about 20 seconds to about 150 seconds, and still more preferably from about 25 to about 100 seconds. Application of these times tends to decrease the amount of catalyst required for the process, enabling reduced catalyst inventories. Such inventories, in turn, provide the advantage of reducing operating and capital costs, in comparison with some prior art processes.

At the provided catalyst residence times and average contact times in the dehydrogenation reactor, the applied temperature of the reaction mixture, which may be supplied in major part by the hot fresh or reactivated catalyst, is desirably from about 500° C. to about 800° C., preferably from about 550° C. to about 760° C., and still more preferably from about 600° C. to about 760° C. Those skilled in the art will understand that the dehydrogenation reaction of the aforementioned C3-C4 hydrocarbon feed is inherently endothermic and that some flexibility within these temperature ranges may in some instances be obtained by appropriate modification of other variables according to the needs of a facility's overall process design.

Temperatures will also be affected by the type of dehydrogenation reactor used in the inventive process. A variety of types may be utilized, provided such offer fluidized contact between the starting C3-C4 hydrocarbon feed and the catalyst feed. Examples of suitable reactor types may include a concurrent or countercurrent fluidized reactor, a riser reactor, a downer reactor, a fast fluidized bed reactor, a bubbling bed reactor, a turbulent reactor, or a combination thereof. In one preferred embodiment, the reactor is a combination of a fast fluidized bed or turbulent reactor in its lower portion, and a riser reactor in its upper portion. In another embodiment a fast fluidized or turbulent reactor may be connected to a separate riser reactor via a frustum. The reactor may be, in certain embodiments, a hot wall reactor or a cold wall reactor, and in either case it may be refractory-lined. It may be manufactured of conventional materials used in fluid catalytic cracking (FCC) or petrochemical processing, such as, for example, stainless steel or carbon steel, and is desirably of a quality capable of withstanding the processing variables including temperature, pressure and flow rates. In particular embodiments, wherein the reactor is a fluidized reactor having concurrent rising flow, the highest temperature in the dehydrogenation reactor will be found at its lower end and, as reaction proceeds and the catalyst and reaction mixture ascends, the temperature will decrease in a gradient toward the upper end of the reactor. See, for example, U.S. Pat. No. 8,669,406 (B2) the disclosure of which is incorporated herein by reference in its entirety. The dimensions of the reactor are generally dependent upon the process design of the applicable facility, and such will generally take into account the proposed capacity or throughput thereof, the weight hourly space velocity (WHSV), temperature, pressure, catalyst efficiency, and unit ratios of feed converted to products at a desired selectivity.

In more particular embodiments the reactor may comprise two definable sections, such that the lower section may operate in a manner that is or approaches isothermal, such as in a fast fluidized or turbulent upflow reactor, while the upper section may operate in more of a plug flow manner, such as in a riser reactor. For example, in the previously described particular embodiment, the dehydrogenation reactor may comprise a lower section operating as a fast fluidized or turbulent bed and the upper section operating as a riser reactor, with the result that the average catalyst and gas flow moves concurrently upward. As the term is used herein, "average" refers to the net flow, i.e., the total upward flow minus the retrograde or reverse flow, as is typical of the behavior of fluidized particles in general.

The applicable operating pressure of the dehydrogenation reactor is broad, enabling optimization based, in embodiments wherein the inventive process is applied in a retrofitted plant, upon applicable economics as allowed for by any existing equipment that will be used for the retrofit. This will be well within the general understanding of the skilled practitioner. In general the pressure may range from 6.0 to 44.7 pounds per square inch absolute (psia, from about 41.4 kilopascals, kPa, to about 308.2 kPa), but it is preferred for most embodiments that a narrower selected range, from 15.0 psia to 35.0 psia, (from about 103.4 kPa to about 241.3 kPa), be employed, more preferably from 15.0 psia to 30.0 psia (from about 103.4 kPa to about 206.8 kPa), still more preferably from 17.0 psia to 28.0 psia (from about 117.2 kPa to about 193.1 kPa), and most preferably from 19.0 psia to 25.0 psia (from about 131.0 kPa to about 172.4 kPa). Unit conversions from standard (non-SI) to metric (SI) expressions herein include "about" to indicate rounding that may be present in the metric (SI) expressions as a result of conversions.

The WHSV for the inventive process may conveniently range from about 0.1 pound (lb) to about 100 lb of C3-C4 hydrocarbon feed per hour (h) per lb of catalyst in the reactor (lb feed/h/lb catalyst). For example, where a reactor comprises a lower portion that operates as a fast fluidized or turbulent reactor and an upper portion that operates as a riser reactor, the superficial gas velocity may range therein from about 2 feet per second (ft/s, about 0.61 meters per second, m/s) to about 80 ft/s (about 24.38 m/s), preferably from about 3 ft/s (about 0.91 m/s) to 10 ft/s (about 3.05 m/s), in the lower portion of the reactor, and from 30 ft/s (about 9.14 m/s) to about 70 ft/s (about 21.31 m/s) in the upper portion of the reactor. In alternative but less preferred embodiments, a reactor configuration that is fully of a riser type may operate at a single high superficial gas velocity, for example, in some embodiments at least 30 ft/s (about 9.15 m/s) throughout.

In the present invention the ratio of catalyst feed to C3-C4 hydrocarbon feed ranges from about 5 to about 100 on a weight to weight (w/w) basis. Preferably the ratio ranges from about 10 to about 40; more preferably from about 12 to about 36; and most preferably from about 12 to about 24. These ratios, which are relatively high in comparison with, for example, a process such as the OLEFLEX™ process, help to ensure, first, that there is sufficient reaction heat generated to drive the inherently endothermic dehydrogenation reaction within the given applied temperature range, and second, that there is sufficient catalyst activity within the reactor to ensure the desired conversion.

It is noted that, in embodiments such as in the two-part reactor described hereinabove, the catalyst flux is preferably from about 1 pound per square foot-second (lb/ft$^2$-s) (about 4.89 kg/m$^2$-s) to about 20 lb/ft$^2$-s (to about 97.7 kg/m$^2$-s) in the lower portion of the reactor, and from about 10 lb/ft$^2$-s (about 48.9 kg/m$^2$-s) to about 100 lb/ft$^2$-s (about 489 kg/m$^2$-s) in the upper portion of the reactor. In a downer reactor, a catalyst flux of higher than about 100 lb/ft$^2$-s (about 489 kg/m$^2$-s) may be employed, but is generally not preferred. Those skilled in the art will be able to appropriately adjust catalyst flux based upon a combination of WHSV and ratio of catalyst feed to C3-C4 hydrocarbon feed. As appears with respect to other conversions from standard (non-SI) to metric (SI) expressions, metric (SI) expressions herein include "about" to indicate rounding resulting from unit conversions.

The catalyst is preferably moved pneumatically through the relevant steps of the inventive process by a carrier fluid, which is preferably an inert diluent fluid. Suitable inert diluent carrier gases may include, for example, nitrogen; volatile hydrocarbons such as methane and other hydrocarbons which do not interfere with the desired dehydrogenation reaction or the catalyst reactivation subprocess, discussed hereinbelow; carbon dioxide; steam, argon; combinations thereof; and the like. The amount of carrier gas employed is preferably limited to approximately the amount necessary to maintain the catalyst particles in a fluidized state and to transport the catalyst from the regenerator to the reactor. Preferably, the amount of carrier gas employed is less than or equal to about 0.2 kilogram of gas per kilogram of catalyst (kg gas/kg catalyst). Injection of the carrier gas may be located at multiple points along a transfer line used to move the catalyst feed, which may include fresh and/or reactivated catalyst, from the regenerator (discussed in greater detail hereinbelow) into the reactor at its lower end. The carrier gas will then desirably exit the dehydrogenation reactor with the step (1)(b) product mixture or through the vent stream of the regenerator.

To summarize step (1)(a) then, the selected C3-C4 hydrocarbon feed may be introduced to the dehydrogenation reactor, which in preferred embodiments is of a bubbling, turbulent, fast fluidized and/or riser design, where it contacts the hot fresh or reactivated catalyst feed, which has been pneumatically moved by a carrier gas to enter the dehydrogenation reactor at a location proximal to that of the C3-C4 hydrocarbon feed. As the catalyst is fluidized in the cylindrical reactor with the C3-C4 hydrocarbon feed, the dehydrogenation reaction takes place and the step (1)(a) product mixture forms. This step (1)(a) product mixture comprises, in a particularly preferred embodiment, at least the target olefin or di-olefin and the hydrogen produced by the dehydrogenation, and often unreacted C3-C4 feed, as well.

At this point, the other sub-process carried out as part of step (1), reaction and catalyst reactivation, begins. The separation of the step (1)(a) product mixture and the catalyst is conveniently accomplished by transfer of the step (1)(a) product mixture and the catalyst to a cyclonic separation system. Cyclonic separation systems are known in the art and may include one stage or two or more stages of cyclonic separation, and one or more than one cyclonic separation device may be employed. Where more than one cyclonic separation device is present, the first cyclonic separation device into which the fluidized stream enters is referred to as a primary cyclonic separation device. The fluidized effluent from a primary cyclonic separation device may enter into a secondary cyclonic separation device. Primary cyclonic separation devices are known in the art and include, for example, primary cyclones, and systems commercially available under the names "VSS" (U.S. Pat. No. 4,482,451), "LD$^2$" (U.S. Pat. No. 7,429,363), and "RS$^2$". Primary cyclones are described in, for example, U.S. Pat. Nos. 4,579,716; 4,588,558; 5,190,650; and 5,275,641. In some known separation systems utilizing primary cyclones as the primary cyclonic separation device, one or more sets of additional cyclones, e.g., secondary cyclones and tertiary cyclones, are employed for further separation of the catalyst from the product gas. It will be understood that any primary cyclonic separation device may be used in embodiments of the invention. In one particular embodiment a two-stage or three-stage solid-gas impingement separator may be selected, and in general two or more stages of cyclonic separation are preferred.

In accomplishing the separation it is highly desirable to substantially reduce or halt the dehydrogenation reaction that will otherwise continue between the catalyst and some or all of the components of the step (1)(a) product mixture. In order to do this, at least one of the following is desirable: (a) the catalyst may be physically separated from the step (1)(a) product mixture as rapidly as possible, which minimizes contact time; and/or (b) the catalyst and/or the step (1)(a) product mixture may be cooled to a temperature below the reaction (dehydrogenation) temperature, that temperature being preferably monitored by a thermocouple located in the process stream just prior to where separation of the catalyst and step (1)(a) product mixture occurs, and/or just following the location where quenching of the catalyst and step (1)(a) product mixture occurs, as previously discussed hereinabove. It is important to understand that, as a result of a certain amount of contact between the catalyst and the step (1)(a) product mixture during transfer to and/or within the cyclonic separation system, the step (1)(a) product mixture will have been converted to a step (1)(b) product mixture. This step (1)(b) product mixture will have certain similar components to the step (1)(a) product mixture, but will include more undesirable by-products as compared to the step (1)(a) product mixture. In addition, the proportion of unreacted C3-C4 hydrocarbon feed obtained from the initial C3-C4 hydrocarbon feed is anticipated to be somewhat reduced. Thus, the separation of the catalyst that is ultimately carried out in the cyclonic separation system is understood to be from the step (1)(b) product mixture. This separation is desirably "substantial," which as used herein means that at least about 90 wt % of the catalyst is separated from the step (1)(b) product mixture, and preferably at least about 95 wt %. In particularly preferred embodiments at least about 98 wt % of the catalyst is separated out.

In addition to separating the catalyst and the step (1)(b) product mixture, the cyclone separation system may be preceded by or may include a heat exchanger and/or quenching unit for delivering a fluid to cool the catalyst and/or step (1)(b) product mixture to a temperature below the reaction temperature. As previously noted hereinabove, another thermocouple is desirably employed immediately prior to such heat exchange and/or quenching step, because at this point the temperature desirably drops below the reaction temperature. In view of this event, the "contact time at temperature" limitations expressed hereinbelow can be ensured, i.e., the "reaction clock" is effectively stopped by the quenching and/or heat exchange procedure. A suitable quenching and/or heat exchange fluid may be delivered via a conventional quenching design including pressurized nozzles for delivering quenching fluid, which may be, for example, a liquid hydrocarbon, such as, but not limited to, benzene, toluene, and/or naphtha; water (liquid or vapor); or the like. Such quenching technology is known to those skilled in the art and may be available from, for example, Stone & Webster Construction Services LLC or BP plc. Cold catalyst may also or alternatively be used as a quench fluid.

It is preferred that the average contact time between the catalyst and step (1)(a)/step (1)(b) product mixture, at reaction temperature, in the separation device is less than about 60 seconds, more preferably less than about 10 seconds, still more preferably less than about 5 seconds, and most preferably less than about 3 seconds, in order to reduce formation of degradation products or by-products that will become part of the step (1)(b) product mixture. It is further preferred that the total average contact time between the catalyst and step (1)(a)/step (1)(b) product mixture at reaction temperature, including both time fluidized within the dehydrogenation reactor wherein the step (1)(a) product mixture is formed, and time in the separation device wherein the step (1)(b) product mixture is formed, is less than about 60 seconds, more preferably less than about 20 seconds, still more preferably less than about 10 seconds, and most preferably less than about 7 seconds. Adherence to these time parameters helps to achieve several benefits, including driving the equilibrium reaction to increase conversion, improving the selectivity, reducing by-product formation, reducing C3-C4 hydrocarbon feed and product degradation, and ensuring and supporting appropriate catalyst reactivation.

Following separation of the catalyst and either the step (1)(a) or step (1)(b) product mixture, the catalyst, which is often colloquially referred to as "spent catalyst," but which is hereinafter referred to as "at least partially deactivated catalyst," may next undergo one of three potential sub-steps. These include (a) stripping, which is optional but often preferred; and/or (b) reactivation, which, although it will theoretically occur to each catalyst particle on a regular basis, may or may not actually occur in any one process cycle. Thus, in an indeterminate number of repeated process cycles, it is understood that a portion of the at least partially deactivated catalyst will likely be simply (c) returned, as it is, directly to the dehydrogenation reactor, or else premixed with regenerated catalyst before the regenerated catalyst enters the reactor. This is preferably via a catalyst return line which may be at various locations in the reactor, but in designs wherein the catalyst flow will be generally (i.e., will average) upward, it is desired that the catalyst be returned at a relatively low point in the reactor, while in designs wherein catalyst flow will be generally (i.e., will average) downward, it is desired that the catalyst be returned at a relatively high point in the reactor. In preferred embodiments of the invention use of (a) stripping, is desirable, because it enables removal of valuable hydrocarbons from the catalyst, and the stripper, if selected, may be employed as a prelude to either or both of (b) the regenerator, or (c) return of the as-is catalyst back to the dehydrogenation reactor.

In particularly desirable embodiments, i.e., in some cycles of the invention's process when practiced in a continuous manner, and as already noted hereinabove, a portion of the at least partially deactivated catalyst, which may or may not have been stripped, is sent to a regenerator. The purpose of the regenerator is two-fold: (1) to provide heat to substantially remove, or "burn off," coke which is deposited on the catalyst as a result of the dehydrogenation reaction, and (2) to provide heat to "reactivate" the catalyst. While the art may employ a variety of alternative terms for reactivation, such as rejuvenation and regeneration, each of these will be understood by those skilled in the art to be used or useful, interchangeably, to refer to treating to increase, enhance, and/or restore the capability of a catalyst to induce or promote a given, desired reaction, which in the present invention, is a dehydrogenation. This is generally understood to refer to the fact that most catalysts significantly lose that capability, i.e., "activity," over time and/or with repeated usage. Thus, it should not be contradictory or confusing to read, for example, that the catalyst can be reactivated in a device referred to as a "regenerator."

In the regenerator the at least partially deactivated catalyst is heated to a temperature of at least 660° C. but no greater than 850° C., preferably from 700° C. to 770° C., and more preferably from 720° C. to 750° C. Again, as for the dehydrogenation reactor, it is preferred that the combustor, which serves as a part of the regeneration area and wherein the coke will be combusted (i.e., oxidized with an oxygen-containing gas) to form $CO_2$, comprises a lower section operating as a fast fluidized, turbulent, or bubbling bed, and an upper section operating as a riser. This enables the combustor to operate with an average catalyst and gas flow moving concurrently upward. Another possible configuration, designed instead to enable an average catalyst flow downward and an average gas flow upward, comprises a fast fluidized, turbulent, or bubbling bed. Regardless of configuration, heat for the regenerator's combustion comes from a combination of (1) combustion of the deposited coke, i.e., the coke itself supplies heat as a result of the oxidation reaction, which further, and cyclically, combusts more coke; and (2) combustion of a supplemental fuel. As the term is used herein, "supplemental" means fuel other than the coke itself. This heating of the catalyst in the combustor results in formation of a heated, further deactivated catalyst, which has an activity for dehydrogenating the selected C3-C4 hydrocarbon feed to produce the target olefin or target di-olefin that is less than that of the at least partially deactivated catalyst. At this point the catalyst can be termed "the further deactivated catalyst."

A particular benefit of the invention is that the same catalyst that carries out the dehydrogenation reaction and is reactivated in the regenerator also provides a certain amount of catalytic, i.e., low temperature, combustion of the coke that is part of the reactivation process. This ensures that all of the coke combustion can be accomplished at the relatively low temperature of no greater than 850° C., rather than at relatively high ("flame," alternatively termed "thermal") combustion temperatures in excess of 1200° C. and often in excess of 1500° C. The substantial use of low temperature combustion offers the particular benefits of improving process economics in general due to lower overall energy costs, and also reducing formation of environmentally undesirable NOx (nitrogen oxides) gases. In preferred embodiments, such NOx gases are formed in amounts that are significantly less per British Thermal Unit (BTU) of fuel than would be produced at temperatures in excess of 1200° C., and more typically in excess of 1500° C. In comparison with processes where 100% of the heat is the result of thermal combustion, a preferred embodiment of the inventive process produces NOx at a level which is reduced by at least 5%, more preferably by at least 10%, still more preferably at least 20%, and most preferably by at least 30%, per BTU of fuel combusted, in comparison with combustion of the same amount of coke, under otherwise identical conditions, but at a temperature in excess of 1200° C. In some cases, the inventive process's NOx reduction can be by as much as 90%, based upon pounds (lb) NOx per BTU of fuel combusted. Evidence of the importance of this emissions reduction may be found in the fact that, for example, the Best Achievable Control Technology (BACT) for the State of Texas, United States, is currently set at 0.036 lb NOx per million ("MM" in standard (non-SI) usage) BTU of fuel combusted for process heaters. That level is generally understood by those skilled in the art to be typical of high (flame) temperature combustion processes.

Following heating, the further deactivated catalyst is desirably subjected to a conditioning step. The conditioning also occurs within the regeneration area of the process and may be accomplished in a reactivation zone comprising, for example, a fast fluidized, turbulent, or bubbling bed. In a particularly preferred embodiment, the reactivation zone configuration enables an average catalyst flow downward and an average gas flow upward, i.e., flows corresponding to those in the combustor, but other configurations are also possible. This conditioning step may comprise maintaining the heated, further deactivated catalyst at a temperature of at least 660° C., but no more than 850° C., preferably from 700° C. to 770° C., and more preferably from 720° C. to 750° C., while exposing it to a flow of an oxygen-containing gas. The conditioning is preferably carried out such that the catalyst has an average catalyst residence time in the oxygen-containing gas of more than 2 minutes, more preferably from 2 minutes to 14 minutes, such that the further deactivated catalyst is converted to an oxygen-containing reactivated catalyst having an activity for dehydrogenating the selected paraffin or olefin that is greater than that of the further deactivated catalyst and, more particularly, of the at least partially deactivated catalyst. This reactivated catalyst may then be cycled back to the dehydrogenation reactor. Optionally, the reactivated catalyst may be stripped, using a gas that does not contain more than 0.5 mole percent (mol %) oxygen, to remove oxygen-containing gas molecules residing between the catalyst particles and/or inside of the catalyst particles.

In another embodiment, a portion of the at least partially deactivated catalyst may also or alternatively be cycled back to the regenerator combustor directly without reactivation, with reactivation, or with partial reactivation, via a recycle loop. The recycled catalyst can be removed at different heights in the reactivation section as desired. It is within the general understanding of the art that the combination of recycled and at least partially deactivated catalyst feed to the combustor may be optimized based upon feedback from the output of the combustor.

In another embodiment, a portion of the at least partially deactivated catalyst may also or alternatively be cycled back to the dehydrogenation reactor directly without any reactivation, via a recycle loop. Recycled, at least partially deactivated catalyst may also be combined with at least partially reactivated catalyst as a means of controlling temperature and catalyst activity prior to catalyst introduction to the dehydrogenation reactor. It is within the general understanding of the art that the combination of recycled and at least partially reactivated catalyst may be optimized preferably upon a combination of feedback from the output of the dehydrogenation reactor and testing of sampled catalyst. To test sampled catalyst, whether fresh, partially deactivated, further deactivated, and/or at least partially reactivated, to determine the activity level thereof, and in particular to optimize reactivation, it is typically convenient to obtain small amounts of catalyst from a variety of process locations and subject these to laboratory scale dehydrogenations. Activity levels can be determined therefrom and appropriate process flow adjustments made.

Figure 1:
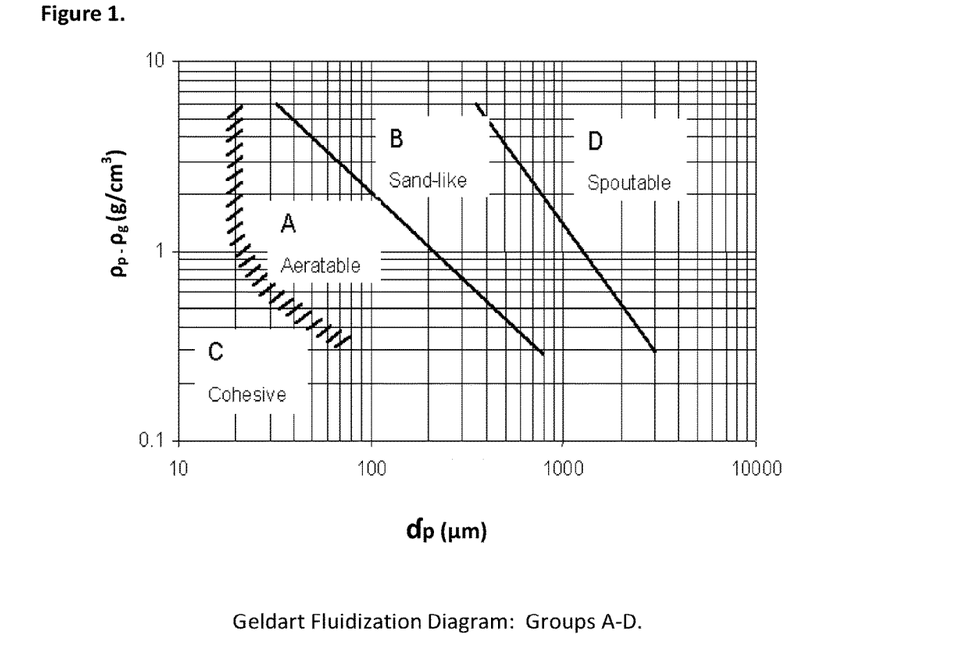
FIG. 1 is a Geldart fluidization diagram.

Preferred catalysts for use in the present invention are relatively very active and are capable of dehydrogenating the selected C3-C4 hydrocarbon feed usually in less than a few seconds at dehydrogenation reaction temperatures. Catalyst selection to meet the reaction time preferences is therefore important to ensuring that the benefits of the short contact time, including driving the equilibrium reaction to increase conversion, improving the selectivity, reducing by-product formation and product degradation, and ensuring and supporting appropriate catalyst reactivation, can be achieved. These preferred catalysts include solid particulate types which are capable of fluidization and, preferably, those which exhibit properties known in the industry as "Geldart A" properties. In addition Geldart B catalyst may also be used, though such may be, in some embodiments, less preferred. These catalysts are classified as "Group A" or "Group B" according to D. Geldart, *Gas Fluidization Technology*, John Wiley & Sons (New York, 1986), 34-37; and D. Geldart, "Types of Gas Fluidization," *Powder Technol.* 7 (1973) 285-292, which are incorporated herein by reference in their entireties. Those skilled in the art will be familiar with the categorization of particles based upon their mean particle size ($d_p$) and particle density ($\rho_p$) under ambient conditions, which determines their fluidization behavior in a given carrier, but for further understanding herein, FIG. 1, generally termed a simplified "Geldart fluidization diagram," as published in 1973 in D. Geldart, "Types of Gas Fluidization," cited supra, is provided. The four Geldart "Group" classifications, A-D, are shown in FIG. 1, with the groups applicable to the inventive process, Groups A and B, generally termed therein as "aeratable" and "sand-like," respectively.

Group A is understood by those skilled in the art as representing an aeratable powder, having a bubble-free range of fluidization; a high bed expansion; a slow and linear deaeration rate; bubble properties that include a predominance of splitting/recoalescing bubbles, with a maximum bubble size and large wake; high levels of solids mixing and gas backmixing, assuming equal $U-U_{mf}$ (U is the velocity of the carrier gas, and $U_{mf}$ is the minimum fluidization velocity, typically though not necessarily measured in meters per second, m/s, i.e., there is excess gas velocity); axisymmetric slug properties; and no spouting, except in very shallow beds. The properties listed tend to improve as the mean particle size decreases, assuming equal $d_p$; or as the <45 micrometers (μm) proportion is increased; or as pressure, temperature, viscosity, and density of the gas increase. In general, the particles exhibit a small mean particle size and/or low particle density (<~1.4 grams per cubic centimeter, g/cm$^3$), fluidize easily with smooth fluidization at low gas velocities, and exhibit controlled bubbling with small bubbles at higher gas velocities.

Group B is understood by those skilled in the art as representing a "sand-like" powder that starts bubbling at $U_{mf}$; that exhibits moderate bed expansion; a fast deaeration; no limits on bubble size; moderate levels of solids mixing and gas backmixing, assuming equal $U-U_{mf}$; both axisymmetric and asymmetric slugs; and spouting in only shallow beds. These properties tend to improve as mean particle size decreases, but particle size distribution and, with some uncertainty, pressure, temperature, viscosity, or density of gas seem to do little to improve them. In general, most of the particles having a particle size ($d_p$) of 40 μm<$d_p$<500 μm when the density ($\rho_p$) is 1.4<$\rho_p$<4 g/cm$^3$, and preferably 60 μm<$d_p$<500 μm when the density ($\rho_p$) is 4 g/cm$^3$ and 250 μm<$d_p$<100 μm when the density ($\rho_p$) is 1 g/cm$^3$. These particles fluidize well with vigorous bubbling action and bubbles that grow large.

It is noted that a variety of closely-related but alternative definitions of the Geldart Groups are provided in additional literature articles, and that powder technology is considered to be an active field of research, but the above definitions as provided herein are generally applicable to the present invention and the scope thereof.

Suitable examples of the defined catalysts include gallium-based catalysts such as those described in U.S. Pat. No. 6,031,143 and WO2002/096844, the disclosures of which are incorporated herein by reference in their entireties. One such catalyst that may be prepared such that it meets the Geldart A or Geldart B definition comprises gallium and platinum supported on alumina in the delta or theta phase, or in a mixture of delta and theta phases, or theta and alpha phases, or delta, theta, and alpha phases, modified with silica, and having a surface area preferably less than about 100 square meters per gram ($m^2/g$), as determined by the Brunauer-Emmett-Teller (BET) method. In preferred embodiments, the catalyst comprises:

i) from 0.1 to 34 wt %, preferably 0.2 to 3.8 wt %, of gallium oxide ($Ga_2O_3$);
ii) from 1 to 300 parts per million (ppm), preferably 50 to 300 ppm, by weight platinum;
iii) from 0 to 5 wt %, preferably 0.01 to 1 wt %, of an alkaline and/or earth-alkaline metal such as potassium;
iv) from 0.08 to 3 wt % silica;
v) the balance to 100 wt % being alumina.

Similar gallium-based catalysts, further comprising manganese, are described in greater detail in WO 2003/053567; U.S. Patent Publication 2004/02242945, which further includes zinc; and in EP 0637578 (B1). The descriptions of the catalysts in these documents are expressly incorporated herein in their entireties by reference.

Another suitable catalyst for the dehydrogenation reaction is based on chromium and comprises:

i) from 6 to 30 weight percent (wt %), preferably, from 13 to 25 wt %, of chromium oxide ($Cr_2O_3$);
ii) from 0.1 to 3.5 wt %, most preferably, from 0.2 to 2.8 wt %, of stannous oxide (SnO);
iii) from 0.4 to 3 wt %, most preferably, from 0.5 to 2.5 wt %, of an alkaline metal oxide, for example, potassium oxide;
iv) from 0.08 to 3 wt % silica;
v) the balance to 100 wt % being alumina in the delta phase; the theta phase; a mixture of delta and theta phases; a mixture of theta and alpha phases; or a mixture of delta, theta, and alpha phases.

The catalysts described hereinabove can be used as-is or in combination with one or more additional materials, such as an inert material, for example, alpha-alumina, and/or modified with oxides of alkaline metals and/or silica, at a concentration of the inert material ranging from 0 to 50 wt %.

Those skilled in the art will be familiar with the above catalyst types and how to prepare or commercially obtain them without further instruction. However, additional details on the preparation of the aforementioned catalysts and their more preferred species may be found in, for example, U.S. Pat. No. 6,031,143 and EP 0637578 (B1), the disclosures of which are incorporated herein by reference in their entireties. Typically, the process of preparing the aforementioned dehydrogenation catalysts comprises dispersing precursors of the catalyst metals, for example, solutions of soluble salts of the selected catalyst metals, onto a carrier comprising alumina, silica, or a combination thereof. An example of an applicable dispersion process may comprise impregnating the carrier with one or more solutions containing the precursors of the selected catalyst metals, for example, gallium and platinum, chromium and tin, or the like, followed by drying and calcinations of the impregnated carrier. An alternative method may comprise ion adsorption of the catalyst metals, followed by separation of the liquid portion of the adsorption solution; drying; and activation of the resultant solid by heating.

In another embodiment the carrier may be treated with volatile species of the desired metals. Alkaline or alkaline earth metals may optionally be added as promoters. Where such are employed, co-impregnation of the carrier with the alkaline or alkaline earth metal and the selected catalyst metals (for example, gallium and platinum, or chromium and tin) may be carried out. Alternatively, the alkaline or alkaline earth metal may be added to the carrier prior to dispersion of the selected catalyst metals (such as gallium, etc.), and optionally thereafter, the entire catalyst construction may be calcined.

Other suitable dehydrogenation catalysts, based on iron oxide, are disclosed in EP 1216219, the disclosure of which is incorporated herein by reference in its entirety. These catalysts may comprise:

(i) from 1 to 60 wt %, preferably from 1 to 20 wt %, of iron oxide;
(ii) from 0.1 to 20 wt %, preferably from 0.5 to 10 wt %, of at least one alkaline or alkaline earth metal oxide, more preferably, potassium oxide;
(iii) from 0 to 15 wt %, preferably, from 0.1 to 7 wt %, of at least one rare earth oxide, preferably selected from the group consisting of cerium oxide, lanthanum oxide, praseodymium oxide, and mixtures thereof;
(iv) the complement to 100 wt % of a carrier consisting of a microspheroidal alumina with a diameter selected from those in delta phase; theta phase; a mixture of theta and alpha phases; or a mixture of delta, theta, and alpha phases; the microspheroidal alumina being modified preferably with from 0.08 to 5.0 wt % of silica.

Another applicable dehydrogenation catalyst consists of a mordenite zeolite, as described in U.S. Pat. No. 5,430,211, the disclosure of which is incorporated herein by reference. The mordenite is preferably acid-extracted and thereafter impregnated or ion-exchanged with one or more metals selected from gallium, zinc, and the platinum group metals, more preferably gallium. In this catalyst, the total metal loading typically ranges from 0.1 to 20 wt %.

(2) Compression

Step (2) of the inventive process includes passing the step (1)(b) product mixture to a compressor unit, generally of a crack gas compressor design. In the compressor unit, the step (1)(b) product mixture is compressed one or more times, preferably at least two times and using more than one compressor unit, and in more particular embodiments at least three times, to form a step (2) product mixture. Because the step (2) product mixture exhibits a significant or substantial increase in inherent pressure in comparison with the step (1)(b) product mixture, it is more easily liquefied for separation (i.e., fractionation) purposes.

(3) Separation

In step (3) of the inventive process, the step (2) product mixture passes from the compressor to a product recovery area, referred to herein as a product recovery unit (PRU), to form a final product stream comprising at least a single target C3-C4 olefin or di-olefin fraction. In particular embodiments the PRU may be termed, for example, a "propylene recovery unit" where the particular target product is propylene, etc. The target C3-C4 olefin or di-olefin fraction may be, for example, propylene, butylene [butene], butadiene, isobutene, or a combination thereof, and such may be recovered in a desirable purity depending upon technology employed in the PRU. The product stream may also comprise additional fractions, selected from, for example, an unreacted C3-C4 starting paraffin or starting olefin fraction; a light gas fraction which includes the hydrogen from the dehydrogenation process, methane, inert gases such as nitrogen and carbon monoxide, and optionally by-products lighter than the desired product; a by-products fraction, defined as comprising paraffins and/or olefins having carbon chain lengths that are less than or greater than the carbon chain length of the target C3-C4 olefin or di-olefin;

a hydrogen fraction; a heavies fraction, defined as comprising paraffins and/or olefins having carbon chain lengths that specifically exceed the carbon chain length of the target C3-C4 olefin or di-olefin; and combinations thereof.

In particular embodiments of the inventive process the hydrogen that is present in the step (2) product mixture and in the final product stream, i.e., in the light gas fraction that is separated in the product recovery unit, is desirably not recycled to step (1a) but is, instead, allowed to remain in the light gas fraction. From there it can be fueled or separated as product hydrogen. Because the hydrogen would use a significant portion of the plant's capacity if recycled to the reactor in step (1a), the elimination of hydrogen recycle in the inventive integrated process operates to functionally increase capacity, as well as shift the equilibrium of the dehydrogenation reaction to increase conversion.

In one embodiment of the inventive process an optional step (4) may be included. This optional step (4) comprises recycle of at least a portion of the unreacted C3-C4 starting paraffin or starting olefin fraction from step (3), separation, back into the inventive process at step (1)(a), reaction and catalyst reactivation; or, again, at step (3), separation; or both. These particular recycle options, and particularly recycle back to step (1)(a), serve to improve the economics of the process in comparison with those of processes lacking such recycle. In addition, one or more of the product stream fractions, or portions thereof, from the product recovery unit may optionally be fed to a separate dehydrogenation process within the same plant or within a different plant; or to another product recovery unit wherein separation (i.e., fractionation) occurs to produce new product streams, which are then recycled back to step (1). In other words, a wide variety of product fraction recycle configurations, designed to increase or maximize value obtained, may be employed while still remaining within the teaching and scope of the integrated inventive process. Additionally, at least a portion of a light gas fraction may be recycled from step (3) to the regenerator's combustor in step (1c), wherein it can serve as at least a portion of the supplemental fuel used in the catalyst reactivation.

In comparison with prior art dehydrogenation processes, the inventive integrated process may offer one or more environmental and/or economic advantages. Such may include, in non-limiting example, enhanced olefin or di-olefin production, enhanced plant capacity, reduced catalyst cost, reduced environmental toxicity (depending upon catalyst choice), enhanced reactor life, lengthened catalyst useful life, reduced NOx emissions, reduced energy costs, reduced capital costs, and the like. More particularly, in particular embodiments the inventive integrated process may offer a combination of high conversion and high selectivity, as well as a significant increase in capacity attributable to the process steps described herein. This capacity increase may be enjoyed by either a new facility designed specifically for the inventive integrated process, or in an existing dehydrogenation facility, previously practicing a different process, such as, for example, an OLEFLEX™ or CATOFIN™ process, that has been retrofitted to practice the inventive integrated process. In preferred embodiments, overall plant capacity may be increased by at least 5%, more preferably by at least 10%, in comparison with a plant practicing a different process, wherein hydrogen is recycled from a product stream back to the dehydrogenation reactor(s). More particularly, the inventive integrated process offers advantages over prior art processes that suffer from one or more of the following: (1) Reduced compression and separation capacity to enable hydrogen recycle; (2) inclusion of sulfur injection to reduce coke formation; (3) crack and creep damage to reactors induced by chlorine that is required for catalyst reactivation; (4) the need for large catalyst inventories to supply fixed bed configurations; (5) the need for large amounts of expensive platinum; (6) the need for high frequency and high temperature valves for swapping fixed catalyst beds; and (7) the need for mitigation of NOx, generated by use of flame temperature heat generation, as required by environmental regulations.

Figure 2:
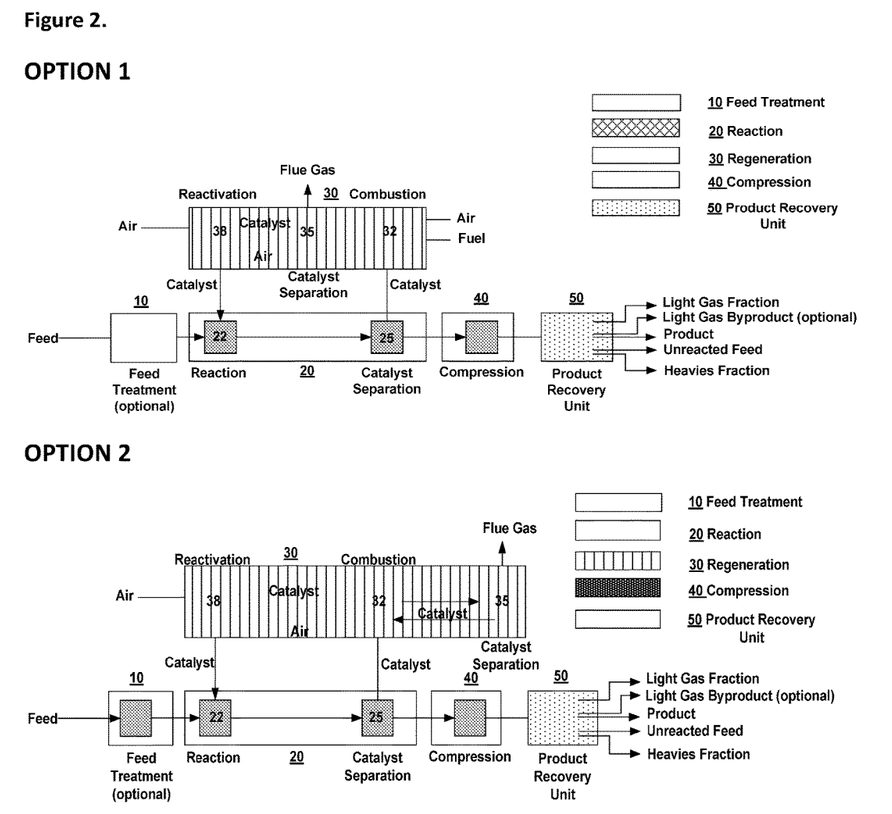
FIG. 2 is a generalized schematic flow diagram showing two embodiments, designated as "Option 1" and "Option 2," of the inventive process, each corresponding to operational units in a hypothetical plant.
Figure 3:
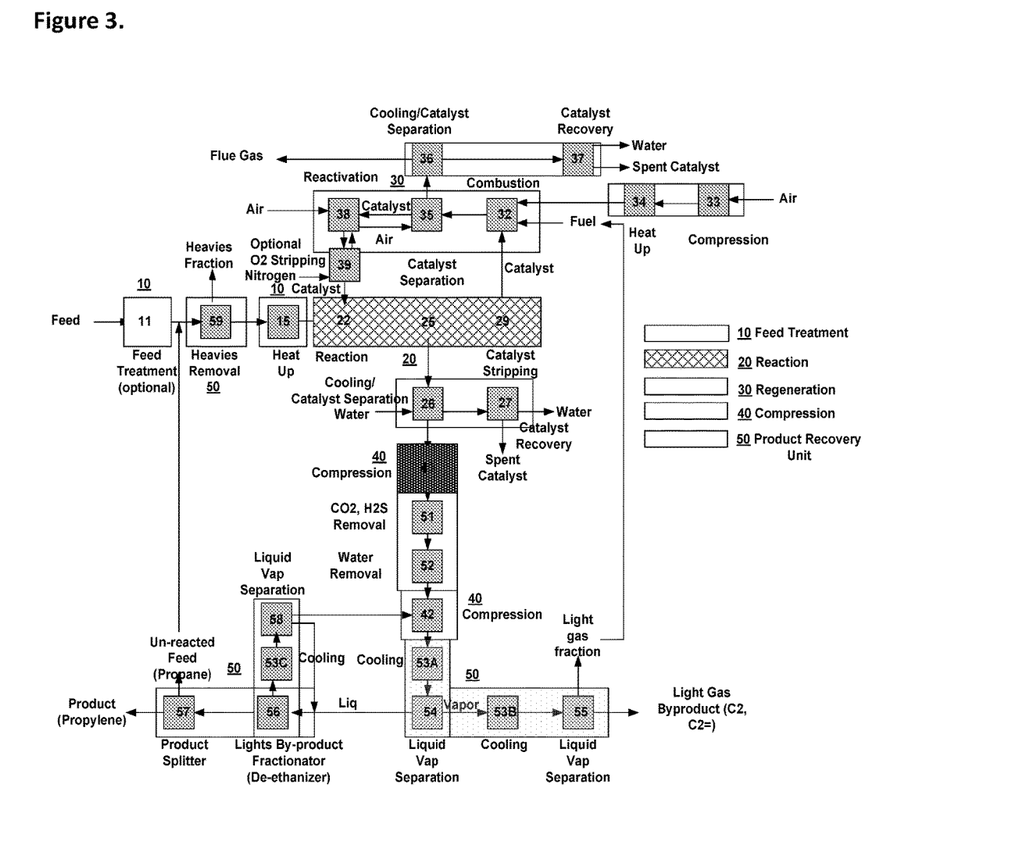
FIG. 3 is a more detailed schematic flow diagram showing one embodiment of the inventive process corresponding to operational areas and units in a hypothetical plant.

Referring now to the FIGS. 2 and 3, the term "unit" refers to what is typically, though not necessarily, a single operational apparatus within a hypothetical plant practicing the inventive process; the term "area" refers to one or more units that together carry out a general function within the inventive process, such as a pre-treatment, a reaction, a compression, a separation, or a recycle; and the term "zone" refers to a specific portion of a unit within which a subfunction occurs, such as a heating, a splitting, or a removal of something previously separated. In the Figures the generalized areas are denoted by the numerals ending in zero (10, 20, 30, 40, and 50), which are underlined, and the corresponding markings as shown in each Figure's key. Units that are part of a given function carry the same initial numeral as the generalized area's initial numeral, but different ending numerals.

FIG. 2 illustrates the inventive process in two different embodiments, designated as "Option 1" and "Option 2." In Option 1, the starting C3-C4 hydrocarbon feed enters the system from the left and is first treated via an optional heating step in a feed treatment area 10. The feed then proceeds to the reaction area 20, where it contacts the catalyst in the dehydrogenation reactor 22 that has entered from a regenerator area 30 and the dehydrogenation of the C3-C4 hydrocarbon (herein termed step (1)(a)) takes place therein. After reaction, the catalyst is separated from the step (1)(a)/step (1)(b) product mixture in the catalyst separation zone 25 and removed to a regenerator area 30. The result of that step (1)(a) dehydrogenation, which because of continued contact with the catalyst and inclusion of the generated hydrogen, is now termed the step (1)(b) product mixture, moves to compression area 40.

Catalyst reactivation takes place by introduction of air and fuel into the combustor 32, which enables combustion to generate heat with supplemental fuel and burn off any deposited coke. The product of combustion, the flue gas, is then separated from the catalyst in the catalyst separation step 35. The catalyst is then contacted with an oxygen-containing gas such as air in the reactivation zone 37. Finally, the fully reactivated catalyst is returned to the dehydrogenation reactor 22 to take part in further dehydrogenation reactions.

Meanwhile, the step (1)(b) product mixture has, as previously mentioned, moved to the compressor area 40 where it is compressed one or more times to form a step (2) product mixture. This compression, herein termed step (2), compression, enables it to be more easily liquefied for later separation purposes.

From the compressor area 40, the step (2) product mixture moves to a product recovery area 50 for step (3), separation. In the product recovery area 50 it is separated into fractions that include at least a desired target olefin or di-olefin product, as well as one or more optional light gas fractions, light gas/by-product fractions, unreacted feed fractions, and heavies fractions, as indicated.

In FIG. 2's "Option 2," the starting C3-C4 hydrocarbon feed enters the system from the left and is first treated via an optional heating step in pre-treatment area 10. The feed then proceeds to the reaction area 20, where it contacts the catalyst, which has entered from a regenerator area 30, in the dehydrogenation reactor 22. The dehydrogenation of the C3-C4 hydrocarbon (in this specification termed step (1)(a)) takes place therein. Following the dehydrogenation reaction, the catalyst is separated from the other components (now the step (1)(b) product mixture) in the catalyst separation zone 25 and then removed to a regenerator area 30. The step (1)(b) product mixture moves to a compression area 40, as discussed further hereinafter.

Continuous catalyst reactivation takes place by introduction of air and fuel into the combustor 32, which enables combustion to generate heat with supplemental fuel and burn off any deposited coke. The product of combustion, the flue gas, is then separated from the catalyst in the catalyst separation step as the catalyst and flue gas are entrained in the catalyst separation system 35. In the Option 2 configuration, the catalyst is continuously entrained, i.e., "looped between," the catalyst separation system 35 and the combustor 32. A portion of this "looped" catalyst is eventually transported to the reactivation zone 37 where it is contacted with an oxygen-containing gas such as air. Finally, the reactivated catalyst is returned to the dehydrogenation reactor 22 to take part in further dehydrogenation reactions.

Meanwhile, the step (1)(b) product mixture has, as previously mentioned, moved to the compression area 40, where it is compressed one or more times to form a step (2) product mixture. This compression, herein termed step (2), compression, enables it to be more easily liquefied for later separation purposes.

From the compression area 40, the step (2) product mixture moves to a product recovery area 50 for step (3), separation. In the product recovery area 50 it is separated into fractions that include at least a desired target olefin or di-olefin product, as well as one or more optional light gas fractions, light gas/by-product fractions, unreacted feed fractions, and heavies fractions, as indicated.

FIG. 3 is a more detailed flow diagram of one embodiment of a plant wherein the inventive process may be practiced, with optional additional features that may be particularly beneficial in certain commercial settings. In particular, optional recycle possibilities are included, which may be particularly useful for increasing plant capacity and/or improving the economics of operation.

In FIG. 3, the starting C3-C4 hydrocarbon feed is treated in the pretreatment area 10 with an optional desulfurizing unit 11. Feed pretreatment can also include heat-up of the feed and/or removal of undesirable molecules such as sulfur molecules, polar molecules such as methanol, and/or other molecules that may negatively impact the catalyst. Water may also be removed in area 10 but, in contrast with the disclosure of U.S. Pat. No. 8,927,799 B2, in the present invention oxygen will be carried over from the regenerator, either between particles or on the catalyst, and water will therefore be formed therefrom in the reactor. It is, therefore, neither necessary nor particularly preferred in the present invention to remove water from the C3-C4 hydrocarbon prior to its introduction into the reactor. In the FIG. 3 embodiment the feed is further augmented, via use of an optional heavies removal column 59, with a proportion of unreacted feed that results from the separation processes occurring in the product recovery area 50, and more particularly in the illustrated embodiment, with propane obtained from a splitter unit 52, from which target propylene is also obtained. In the illustrated embodiment, the heavies removal column 59 is employed at the beginning of the process as shown here, wherein the heavies fraction obtained from the product recovery area 50 may be separated and sent on for further processing. In such embodiment an additional lighter product may be obtained, which may serve as some or all of the C3-C4 hydrocarbon feed that goes back into step (1)(a). In this case it will then progress on to being heated in heating unit 15. In other embodiments, the heavies removal column is either not employed at all, or is employed only at the back end of the process and not for processing the heating unit 15's feed.

In this embodiment, the heated C3-C4 hydrocarbon feed then proceeds to the reaction area 20, where it contacts the catalyst, which has entered from a regenerator unit 30, in the dehydrogenation reactor 22. As in FIG. 2, the dehydrogenation of the C3-C4 hydrocarbon (herein termed step (1)) takes place therein. After reaction, the catalyst is separated from the step (1) product mixture in the catalyst separation zone 25 and then stripped of the entrained step (1) product mixture by means of an effective stripping gas in the catalyst stripping unit 29 prior to its being removed to the regenerator area 30. The result of that step (1) dehydrogenation, now termed the step (1) product mixture, moves to the cooling/separation zone 26. At this location the catalyst is separated from the step (1) product mixture.

Catalyst reactivation takes place by introduction of air and fuel into the combustor 32, which enables combustion to generate heat with supplemental fuel and burn off any deposited coke. The product of combustion, the flue gas, is then separated from the catalyst in the flue gas separation zone 35. The catalyst is then contacted with an oxygen-containing gas such as air in the reactivation zone 38.

The catalyst is then optionally stripped with an inert compound such as nitrogen to remove any entrained oxygen in the oxygen stripping area 39. This step will not, however, remove oxygen on the catalyst surface which, as previously noted, can produce water in the reactor. Finally, the reactivated catalyst is returned to the dehydrogenation reactor 22 to take part in further dehydrogenation reactions.

FIG. 3 also shows, as part of the catalyst reactivation subprocess in the illustrated embodiment of the inventive integrated process, use of an air compressor 33 to generate air at a desired pressure. This air is heated in heating zone 34 prior to introduction into the combustor 32.

The flue gas that exits the flue gas separation zone 35 is cooled and the catalyst is separated in the regenerator's cooling/catalyst separation zone 36 from the flue gas. Finally, the catalyst is recovered in the catalyst recovery zone 37.

Meanwhile and concurrently, the step (1)(b) product mixture passes from the catalyst separation zone 25 to a catalyst cooling/catalyst separation zone 26. The resulting liquid that contains particles is then processed in the catalyst recovery area 27. The step (1)(b) product mixture is then sent to the crack gas compressor 41, which is part of the compression area 40. The crack gas compressor 41 is preferably a two-stage compressor designed to increase the pressure of the step (1)(b) product mixture. The step (1)(b) product mixture may be compressed at least once, then treated to remove $CO_2$ and $H_2S$ in a caustic tower 51, and then the water is removed in a drier 52. The treated gas is then compressed at least once again, in a second crack gas compressor 42. It will be observed in this embodiment that the compression area 40 and product recovery area 50 may be partially overlapped.

The final compressed mixture (termed the step (2) product mixture once it has been compressed) is then cooled in cooling zone 53A. The liquid and vapor are separated in a separation zone 54. The resulting vapor is further cooled in another cooling zone 53B and then separated again in another separation zone 55. The resulting vapor from separation zone 55 is the light gas fraction, which may in some embodiments then be feed to the combustor 32 as fuel. The liquid from separation zone 55 is the light gas by-product.

The liquid from separation zone 54 is then transported to a lights by-product fractionator or deethanizer 56, which is desirably used in the case of propane dehydrogenation. The resulting vapor stream is cooled in cooling zone 53C and sent to a liquid/vapor separator 58. The liquid from separator 58 is recycled to the lights by-product fractionator 56 while the vapor is recycled to crack gas compressor 42.

The liquid from the lights by-product fractionator 56 is then sent to a product splitter 57. In this case, propane is separated from propylene, the final target product. The unreacted propane is then fed to the heavies removal column 59 wherein the molecules heavier than propane will be removed to form a (or an additional) heavies fraction and the resulting propane will ultimately be returned for reaction in the dehydrogenation reactor 22.

The invention claimed is:

1. An integrated process for producing C3-C4 olefins or C3-C4 di-olefins comprising the steps of:
   (1) (a) contacting, in a fluidized dehydrogenation reactor,
      (i) a C3-C4 hydrocarbon feed and
      (ii) a catalyst feed comprising a catalyst meeting the requirements of a Geldart A or Geldart B classification;
      at a ratio of catalyst feed to C3-C4 hydrocarbon feed of from 5 to 100 on a weight to weight basis;
      wherein the average contact time between the C3-C4 hydrocarbon feed and the catalyst feed is from about 1 second to about 10 seconds; and
      wherein the reaction temperature in the fluidized dehydrogenation reactor is from about 550° C. to about 750° C.; and
      wherein the pressure in the fluidized dehydrogenation reactor is from 6.0 to 44.7 pounds per square inch absolute at the outlet of the reactor;
      under conditions such that a step (1)(a) product mixture, comprising a C3-C4 target olefin or di-olefin, hydrogen and unreacted C3-C4 hydrocarbon feed, is formed; and
      the catalyst has coke deposited thereon and is at least partially deactivated such that it forms an at least partially deactivated catalyst; and
   (b) transferring the step (1)(a) product mixture and the at least partially deactivated catalyst from the fluidized dehydrogenation reactor to a cyclonic separation system, and
      under conditions such that
      (i) the step (1)(a) product mixture and the at least partially deactivated catalyst remain in contact, at the reaction temperature and after the transfer to the cyclonic separation system, for an average time of from 0 seconds to less than about 10 seconds, and
      (ii) the step (1)(a) product mixture is converted to form a step (1)(b) product mixture; and
      thereafter substantially separating the step (1)(b) product mixture and the at least partially deactivated catalyst from each other;
   (c) transferring at least a portion of the at least partially deactivated catalyst to a regenerator vessel and heating the at least partially deactivated catalyst therein to a combustion temperature of from about 660° C. to about 850° C. in order to combust the coke deposited on the at least partially deactivated catalyst therein, using heat generated by the coke combustion itself and also by a supplemental fuel,
      the heating forming a heated, further deactivated catalyst which has an activity for dehydrogenating the C3-C4 hydrocarbon feed that is less than that of the at least partially deactivated catalyst, and,
   (d) subjecting the heated, further deactivated catalyst to a conditioning step, comprising maintaining the heated, further deactivated catalyst at a temperature of at least 660° C. under a flow of an oxygen-containing gas for more than 2 minutes,
      to form an oxygen-containing, at least partially reactivated catalyst that has an activity for dehydrogenating the C3-C4 hydrocarbon feed that is greater than that of the at least partially deactivated catalyst; and
   (e) transferring the at least partially reactivated catalyst back to the fluidized dehydrogenation reactor;
   (2) transferring the step (1)(b) product mixture to a compressor, wherein the step (1)(b) product mixture is compressed at least once to form a step (2) product mixture; and
   (3) transferring the step (2) product mixture to a product recovery area,
      wherein the step (2) product mixture is separated into recovered products comprising at least one or more target C3-C4 olefin or di-olefin fractions.

2. The process of claim 1, wherein the catalyst comprises gallium and platinum on an alumina or alumina silica support.

3. The process of claim 1, wherein the C3 hydrocarbon in the C3-C4 hydrocarbon feed is propane and the step (3) product mixture comprises a propylene fraction.

4. The process of claim 1, being retrofitted in a plant previously comprising a reaction system comprising multiple adiabatic reactors arranged in a series.

5. The process of claim 1, being retrofitted in a plant previously comprising a reaction system comprising multiple fixed bed dehydrogenation reactors deployed in parallel.

6. The process of claim 4, wherein the retrofitted plant has a capacity that is at least 5 percent greater than that of a non-retrofitted plant.

7. The process of claim 1, wherein the fluidized dehydrogenation reactor comprises a lower section operating as a fast fluidized or turbulent bed, and an upper section operating as a riser, and wherein the average catalyst flow and the average gas flow are concurrently upward.

8. The process of claim 1, where the combustion in the regenerator occurs in either a combustor comprising a lower section operating as a fast fluidized, turbulent, or bubbling bed, and an upper section operating as a riser, wherein the average catalyst flow and average gas flow are concurrently upward; or in a combustor comprising a fast fluidized, turbulent, or bubbling bed, wherein the average catalyst flow is downward and the average gas flow is upward.

9. The process of claim 1, wherein the conditioning step occurs in a fast fluidized, turbulent or bubbling bed regenerator, wherein the average catalyst flow is downward and the average gas flow is upward.

10. The process of claim 1, wherein hydrogen is not recycled from step (3) to step (1)(a).

11. The process of claim 1 including as an additional step stripping the catalyst between step (1)(b) and step (1)(c).

12. The process of claim 11, wherein:
    the step (2) product mixture is separated into recovered products comprising at least one or more target C3-C4 olefin or di-olefin fractions, and one or more additional fractions selected from an unreacted C3-C4 hydrocarbon feed fraction; a light gas fraction; a heavies fraction; a by-products fraction; and combinations thereof; and wherein at least a portion of the unreacted C3-C4 hydrocarbon feed fraction is recycled back to step (1)(a); and the light gas fraction is transferred to step (1)(c) to serve as the supplemental fuel.

* * * * *